US008611975B2

(12) United States Patent
Gerlitz

(10) Patent No.: US 8,611,975 B2
(45) Date of Patent: Dec. 17, 2013

(54) APPARATUS AND METHOD FOR NON-INVASIVE MEASUREMENT OF A SUBSTANCE WITHIN A BODY

(75) Inventor: Yonatan Gerlitz, Herzliya (IL)

(73) Assignee: Gluco Vista, Inc., Fairfield, NJ (US)

( * ) Notice: Subject to any disclaimer, the term of this patent is extended or adjusted under 35 U.S.C. 154(b) by 941 days.

(21) Appl. No.: 12/607,903

(22) Filed: Oct. 28, 2009

(65) Prior Publication Data

US 2011/0098542 A1   Apr. 28, 2011

(51) Int. Cl.
*A61B 5/00* (2006.01)
*G01J 1/04* (2006.01)
*G01J 1/00* (2006.01)

(52) U.S. Cl.
USPC ............ 600/310; 600/322; 356/236; 250/228

(58) Field of Classification Search
USPC .......... 600/310, 322, 340, 365; 356/215, 236; 250/228
See application file for complete search history.

(56) References Cited

U.S. PATENT DOCUMENTS

| | | | |
|---|---|---|---|
| 3,770,958 A | 11/1973 | Krakow | |
| 5,237,178 A | 8/1993 | Rosenthal et al. | |
| 5,313,941 A | 5/1994 | Braig et al. | |
| 5,370,114 A | 12/1994 | Wong et al. | |
| 5,515,847 A | 5/1996 | Braig et al. | |
| 5,601,079 A | 2/1997 | Wong et al. | |
| 5,615,672 A | 4/1997 | Braig et al. | |
| 5,666,956 A | 9/1997 | Buchert | |
| 5,895,918 A * | 4/1999 | Powell et al. | 250/339.08 |
| 6,647,350 B1 * | 11/2003 | Palfenier et al. | 702/134 |
| 6,949,070 B2 | 9/2005 | Ishler | |
| 6,998,247 B2 | 2/2006 | Monfre et al. | |
| 7,183,102 B2 | 2/2007 | Monfre et al. | |
| 7,308,293 B2 | 12/2007 | Gerlitz | |
| 2002/0016533 A1 * | 2/2002 | Marchitto et al. | 600/310 |
| 2004/0257557 A1 | 12/2004 | Block | |
| 2005/0033186 A1 | 2/2005 | Nordstrom et al. | |
| 2005/0043630 A1 | 2/2005 | Buchert | |
| 2008/0269580 A1 | 10/2008 | Balistreri et al. | |
| 2009/0259407 A1 | 10/2009 | Gerlitz | |

FOREIGN PATENT DOCUMENTS

| | | | |
|---|---|---|---|
| EP | 0160768 A1 | 11/1985 | |
| EP | 1568309 A1 | 8/2005 | |

OTHER PUBLICATIONS

International Search Report dated Mar. 23, 2011 from PCT/US2010/050901 filed Sep. 30, 2010.

* cited by examiner

*Primary Examiner* — Clayton E Laballe
*Assistant Examiner* — Minh Phan
(74) *Attorney, Agent, or Firm* — Parsons Behle & Latimer

(57) ABSTRACT

A method and apparatus for the noninvasive detection of a concentration of a substance in a body, such as glucose in the human bloodstream is disclosed. The apparatus measures substance concentration by detecting radiation in the far infrared range emitted by the body using an infrared detected in combination with a set of adequate filters. In order to achieve the accuracy required, the radiation values detected by the detector are corrected for the emissions of the system components. The temperature of each system component including the detector temperature and an ambient temperate is determined using temperature sensors attached to the various system components. These temperatures are correlated with a set of predetermined calibration parameters to correct the detector readings.

4 Claims, 5 Drawing Sheets

APPARATUS AND METHOD FOR NON-INVASIVE MEASUREMENT OF A SUBSTANCE WITHIN A BODY

BACKGROUND

The present application relates generally to the non-invasive measurement of various substances in a body, such as the measurement of the concentration of glucose in the human body and, more specifically, to a far infrared detection system to analyze and determine, non-invasively, the concentration of a substance in a body.

Spectroscopic techniques using infrared ("IR") radiation are known in the prior art and have been widely used for non-invasive measurement of the concentration of substances of interest in a body. One area of particular interest is the use of these techniques for the non-invasive measurement of the concentration of glucose and other constituents of the human bloodstream.

The infrared spectra includes the near infrared (approximately 1 to 3 microns), the middle infrared (approximately 3 to 6 microns), the far infrared (approximately 6 to 15 microns), and the extreme infrared (approximately 15 to 100 microns). Typical prior art glucose and other non-invasive blood constituent measuring devices operate in the near infrared regions where the absorption of infrared energy by glucose and other blood constituents is relatively low. However, it is known that glucose and other blood constituents have strong and distinguishable absorption spectra in both the middle and far infrared regions.

It has been found in a far infrared detection system that the resolution of the system should be equivalent to $0.01°$ C. to provide sufficiently accurate measurements. At this high level of accuracy, the blackbody emission of any component of the system (mirrors, filters, field limiters, detector, for example) can cause perturbations in the measurement. The conventional solution to such a problem is to cool the system to a cryogenic temperature ($-180°$ C., for example), and have the system sealed and filled with dry nitrogen to avoid moisture accumulation. However, for a consumer product, such a solution is impractical and expensive.

SUMMARY

The present application discloses a far infrared system to analyze and determine, non-invasively, the concentration of a substance in a body. In accordance with one embodiment, an apparatus for the non-invasive measurement of a substance within a body includes a detector for sensing radiation emitted or remitted from a body, a human body, for example. An optical system is provided and aligned to focus IR radiation emitted by the body on a sensitive area of the detector.

Each element of the system within the field of view of the detector and the detector itself has a temperature measuring device such as a thermistor attached to it for the purpose of measuring its temperature. For the detector to accurately measure the energy radiated by the body, the system is calibrated to compensate for the effect of the temperature of each element in the detector field of view. Using a heating or heating/cooling unit for each element separately, the temperature of each element can be varied for the purpose of calibration while the temperatures of the other elements of the system remain stable. This process is repeated many times in various ambient temperatures and various body temperatures in order to calibrate the effect of each element on the measurement in all ranges of conditions relevant for the measurement.

This procedure is repeated for each element in the field of view of the detector yielding a look-up table ("LUT") representing the contribution of each element to the detector's measurement. The perturbations due to the temperature of each of the system elements are taken into account in each measurement, thereby enabling the system to obtain a high level of accuracy.

During the creation and build-up of the LUT, it was found that the temperature effect of a baffle used to limit the field of view of the detector is 10:1 relative to the body reading. Calibration alone cannot compensate for such a significant effect.

The solution in the far infrared region is to reduce the emissivity of the baffle by enhancing its reflectivity. However, enhancing the reflectivity of the baffle creates an additional problem of reflecting stray energy to the detector. A spherical baffle was designed with an internal surface, i.e., the surface of the baffle opposite the detector, that is polished and gold-plated to lower the emissivity. The baffle design eliminates any reflection or multiple reflections from reaching the sensitive area of the detector.

The base plate that the detector and the baffle are mounted on and the baffle have substantially the same temperature as the detector. The base plate and the outer surface of the baffle are designed as a radiation trap having a dull black surface providing an emissivity of about 97%.

The design of the system optics creates an image of the detector sensitive area on the surface of the body in order to collect the IR radiation emitted or remitted from the body. The area on the surface of the body subtended by the image of the detector sensitive area is critical since the detector is averaging the IR radiation emitted or remitted from this area.

In accordance with another embodiment, the present optical apparatus comprises two changeable optical filters, a first mirror positioned to a first side of the optical filter, and a second mirror positioned to a second side of the optical filter opposite the first mirror. A detector is positioned to the second side of the optical filter. A baffle partially surrounds a sensitive surface of the detector. Temperature-measuring devices are configured to measure the temperature of the baffle, mirrors and filters. The first mirror is configured to receive IR radiation from a measured surface of the body, collimate the IR radiation to a beam, and reflect the collimated IR beam toward and through the optical filter. One of the optical filters is configured to filter out a portion of the collimated IR beam having wavelengths that fall outside a selected bandwidth, and the second optical filter is configured to filter out a portion of the collimated IR beam having wavelengths that fall within a selected bandwidth. The filters are changeable by a motorized mechanism, and each IR radiation measurement consists of at least one measurement with one filter and a second measurement with the second filter. The second mirror is configured to receive the collimated and filtered IR beam and reflect it toward the detector. The baffle is configured to block stray IR radiation so that it does not reach the detector sensitive area.

Each of the two radiation measurements is then corrected to eliminate the effect of the emission of the system elements on the measurement. The ratio of the two radiation measurements after the correction and normalization for a black body reading is correlated to the concentration of the desired substance in the body, such as the concentration of glucose in the bloodstream of a human body, for example.

BRIEF DESCRIPTION OF THE DRAWINGS

The following figures, in which like numerals indicate elements, form part of the present specification and are included to further demonstrate certain aspects of the present invention. The invention may be better understood by reference to one or more of these figures in combination with the detailed written description of specific embodiments presented herein.

These and other embodiments of the present application will be discussed more fully in the description. The features, functions, and advantages can be achieved independently in various embodiments of the claimed invention, or may be combined in yet other embodiments.

DETAILED DESCRIPTION

One or more illustrative embodiments are described below. Not all features of an actual implementation are necessarily described or shown for the sake of clarity.

Figure 1:
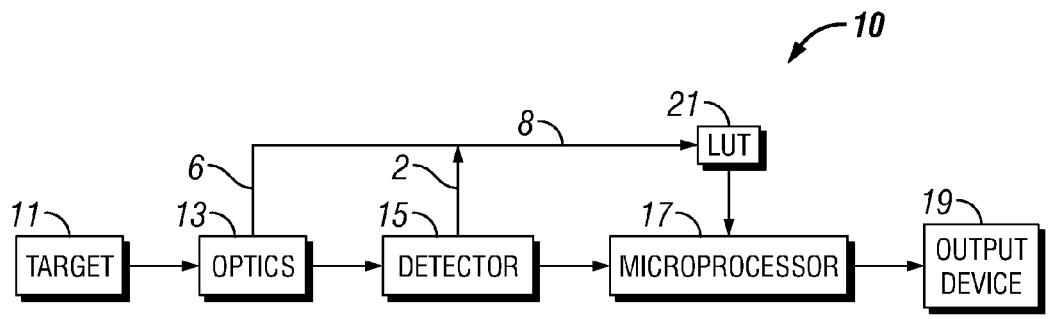
FIG. 1 illustrates a block diagram of a system for the non-invasive measurement of the concentration of a substance in a body.

Referring now to FIG. 1, a block diagram of a system 10 for the non-invasive measurement of the concentration of a substance in a body is shown. Infrared ("IR") radiation emitted or reflected from the surface of a body 11 is collected and collimated by optics subsystem 13 and focused on IR detector assembly 15. The body 11 is the source of the IR radiation being measured by the system 10. The body 11 is typically a portion of a surface of a body of interest, such as a human body, for example. The optical subsystem 13 includes at least two changeable filters 33, 35, as shown in FIG. 2, that allow two different wavelength bandwidth signals, the first including a characteristic wavelength of a desired substance, such as glucose, for example, to be measured, the second being a portion of the emitted radiation not including the substance characteristic wavelength to be used as a reference signal.

Figure 4:
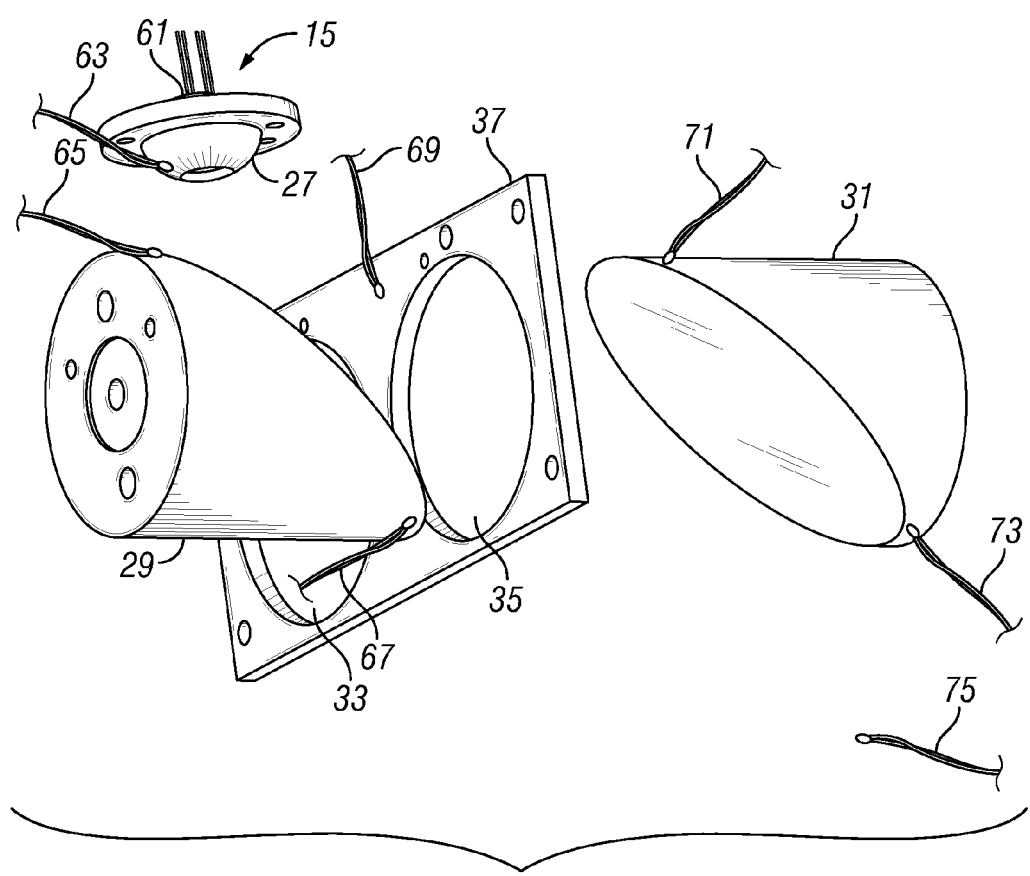
FIG. 4 is a perspective view of the optical and detector apparatus of FIG. 2, showing the locations on the various elements of the optical and detector apparatus of the temperature measurement devices.

The detector assembly 15 senses both signals and provides an output voltage that is proportional to the intensity of each of the two signal measurements to the microprocessor 17. Temperature sensors, as shown in FIG. 4, provide the temperatures of the various optical subsystem and detector assembly components and the ambient temperature to the microprocessor 17 via lines 2, 6, and 8 and a look up table ("LUT") 21. In a calibration process, the temperature of each of the optical subsystem and detector assembly components is varied while the temperature of the remaining system components is held stable to provide a set of calibration parameters that are stored in the LUT 21.

The microprocessor 17 uses the set of predetermined calibration parameters to correct each of the two radiation measurements to eliminate the effect of the emission of the system elements on the measurement. The ratio of the two radiation measurements after the correction and normalization for a black body reading is correlated to the concentration of the desired substance in the body, such as the concentration of glucose in the bloodstream of a human body, for example. The result is then provided to an output device 19, such as an LCD or LED video monitor, for example.

Figure 2:
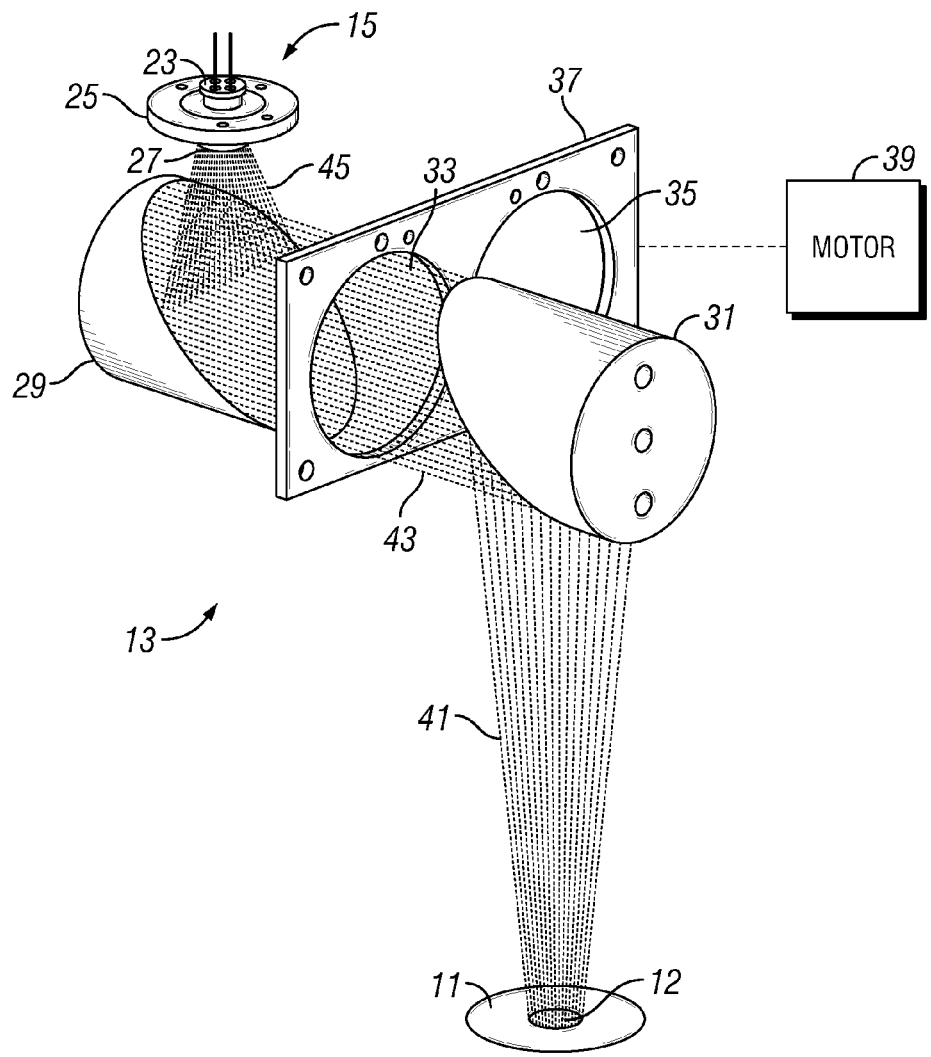
FIG. 2 is a perspective view of the optical and detector apparatus of FIG. 1 illustrating the path of travel for electromagnetic rays between the body and the detector.
Figure 3:
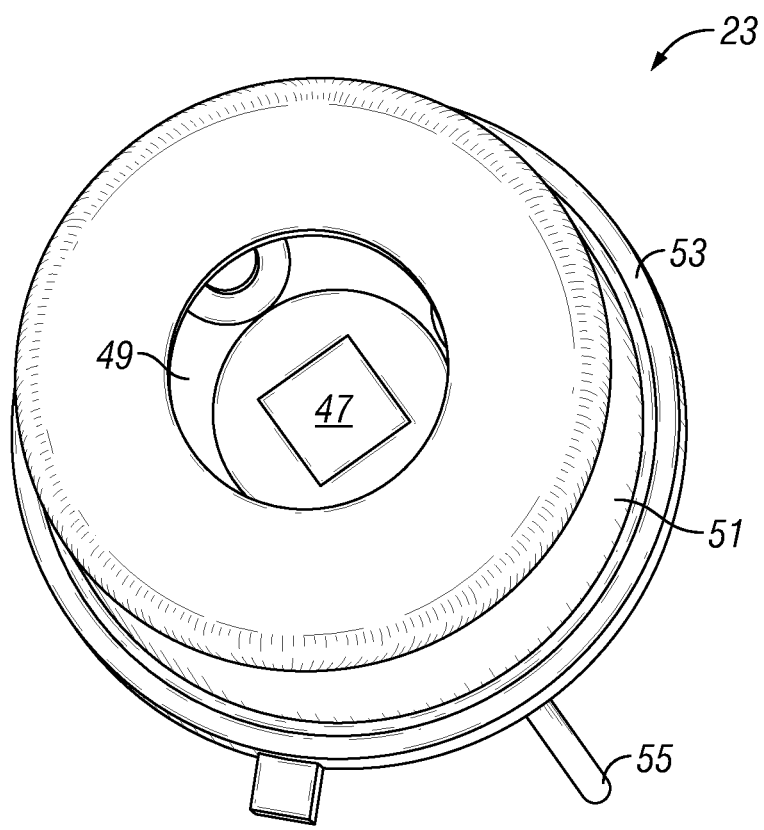
FIG. 3 is a perspective view of the detector of FIGS. 1 and 2.

Referring now also to FIG. 2, a schematic perspective view of the configuration of the optical and detector components of the system 10 shown in FIG. 1, illustrating the path of travel for IR rays between the body 11 and the detector 15 is shown. The detector 15 includes the detector element 23, detector base 25 and a baffle 27. The configuration of the optical and detector components is designed such that an image 12 of the sensitive or active area 47 of the detector 15 (as shown in FIG. 3) is created at the body 11 on the focal plane of mirror 31.

The area of image 12 preferably has a diameter approximately 6 mm. IR radiation emitted from or reflected by the body 11 at image 12 in beam 41 is collected and collimated by mirror 31. The IR radiation is reflected by mirror 31 and propagated to mirror 29 in a collimated beam 43 of parallel rays via filter 33 or filter 35. The focal plane of mirror 29 is located at the surface of the sensitive area 47 of the detector assembly 15. The beam 43 reaching mirror 29 is reflected and propagated as beam 45 and focused at the focal plane of mirror 29 incident on the detector assembly 15 sensitive area 47.

The detector assembly 15 is partially surrounded by a baffle 27 on the side facing the mirror 29. The baffle 27 insures that substantially only beam 45 is incident only on the sensitive area 47. Baffle 27 also blocks any stray radiation from reaching the sensitive area 47 of detector assembly 15. Thus, the optical subsystem 13 is aligned such that the image 12 is positioned at the surface of body 11 and the beam 41 of IR radiation is incident on the sensitive area 47 of detector assembly 15 via mirror 31, filter 33 or filter 35 and mirror 29.

In one embodiment, mirrors 29 and 31 are preferably ninety-degree (90°) off-axis parabolic mirrors coated with gold or other suitable reflective material. Preferably mirror 29 will have a focal length of about one (1) inch and mirror 31 will have a focal length of about three (3) inches. Other suitably designed reflective mirrors may be used for the optical subsystem 13 such as ellipsoid mirrors or a combination of ellipsoid and hyperbolic mirrors, for example.

Filter 33 and filter 35 are mounted in frame 37, frame 37 being positioned between mirror 29 and mirror 31. The filters 33, 35 are switched between positions intercepting the beam 43 using a suitable driving mechanism, such as a motor or pneumatic pressure, for example, coupled to frame 37. In one embodiment, motor 39 is coupled to the frame 37 and positions the frame 37 between the mirror 29 and mirror 31 such that the desired filter 33, 35 intercepts the beam 43. One of the filters, filter 33, for example, will preferably be a narrow band filter passing the wavelengths of the spectral characteristic of the substance being measured. The other filter, filter 35, for example, will preferably be a narrow band filter passing those wavelengths of a spectral characteristic not sensitive to the substance being measured. For example, in some embodiments, filter 33 will limit the bandwidth to that region of the spectrum where there is no emission for the substance being measured (for glucose, for example, the bandwidth would be 10.5μ-15μ), while filter 35 would have a bandwidth characteristic of the emission of the substance being measured (for glucose, the bandwidth would be 8.5μ-10.5μ).

Referring now also to FIG. 3, a perspective view of the detector element 23 shown in FIGS. 1 and 2 is illustrated. Any suitable IR detector responsive to the desired wavelengths of interest may be used. The detector element 23 includes a chip providing the IR sensitive material forming the detector sensitive area 47. The chip, or sensitive area 47, is enclosed in a case 51 and mounted to a base 53. The case 51 has an appropriately-sized opening forming a window 49 in its top surface to allow the IR radiation to reach the sensitive area 47. The window 49 is covered by a material transparent to the radiation of interest, such as silicon or other suitable material. Leads 55 connect the detector element 23 to the microprocessor 17 and other circuitry. In one embodiment, a passive IR sensor known as a thermopile detector is used. Thermopile detectors respond to IR power emitted by an object in its field of view by producing a voltage that is proportional to incident power. One suitable thermopile detector is manufactured by Dexter Research Corporation (part number ST150). The thermopile detector used in one embodiment has a sensitive area 47 with dimensions of 1.5 mm×1.5 mm and a window 49 of silicon.

Referring now also to FIG. 4, a perspective view of the optical subsystem 13 and detector assembly 15 of FIG. 2 is shown, illustrating suitable locations on the various elements of the optical subsystem and detector assembly where temperature measurement devices may be located. Each element of the optical subsystem and detector assembly will emit electromagnetic radiation including IR radiation as a function of its temperature. In order to achieve the resolution necessary to produce an accurate measurement of the desired substance, the emission of each element in the system is preferably taken into account.

Each element of the optical subsystem 13 within the field of view of the detector assembly 15, as well as the detector assembly 15, includes one or more suitable temperature sensing devices mounted at suitable locations on the element to accurately measure the temperature of the element. In one embodiment, thermistors are used as the temperature measuring devices. A thermistor is a temperature dependent resistor typically composed of a semiconductor material. The resistance of a thermistor is inversely proportional to temperature, i.e., as the temperature increases, its resistance decreases. While other suitable temperature sensors can be used, thermocouples, for example, typically a thermistor provides a greater output voltage.

In the embodiment shown in FIG. 4, thermistor 61 is located internally to the detector assembly 15 to measure the temperature of the cold junction where a thermopile detector is used. Thermistor 63 measures the temperature of the baffle 27. Thermistors 65 and 67 measure the temperature of mirror 29, and thermistors 71 and 73 measure the temperature of mirror 31. Two thermistors are used for each mirror due to the size and mass of the mirrors. Thermistor 69 measures the temperature of the filters 33, 35 and of frame 37 assembly. Thermistor 75 measures the ambient room temperature. The temperature of each element is matched with a set of predetermined calibration parameters stored in LUT 21 together with the temperature of detector 15, ambient temperature, and the temperature of body 11, to compensate for any perturbations in a substance concentration measurement due to the temperatures of the various optical subsystem and detector assembly elements.

Figure 5:
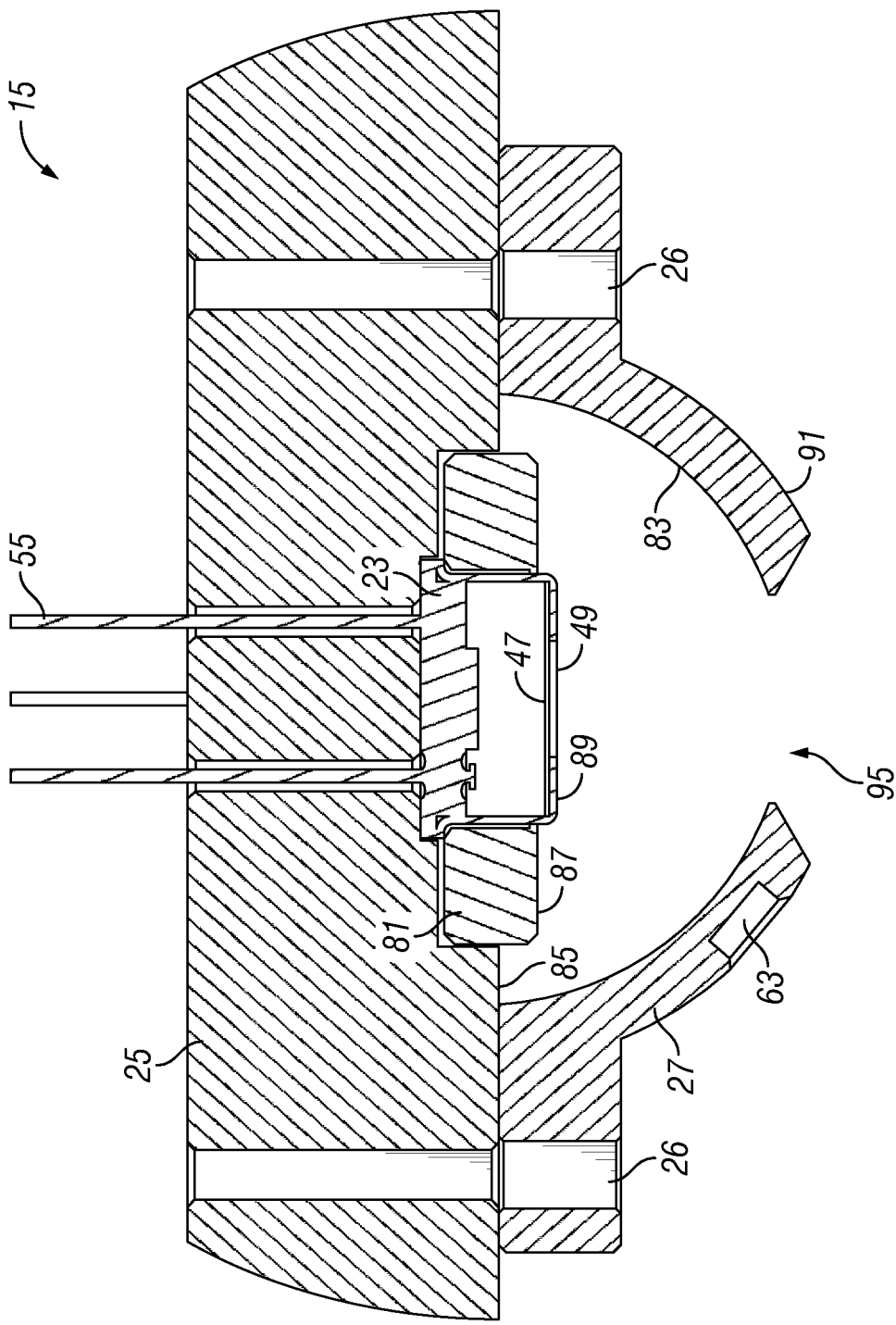
FIGS. 5 and 6 are cross-sectional views of the detector and baffle of the optical and detector apparatus shown in FIG. 2.

Referring now also to FIG. 5, a cross-sectional view of the detector assembly 15 and baffle 27 of the optical and detector apparatus of FIG. 2 is shown. In the illustrated embodiment, detector element 23 is held by a retainer ring 81 in thermal contact with detector base 25. Baffle 27 is attached to the detector base 25 with fasteners 26, establishing good thermal contact between the detector element 23, ring 81, detector base 25, and baffle 27. The inner surface 83 of baffle 27 is preferably gold-coated and polished to create a mirror. The inner surface 83 of baffle 27 is designed to have a very low emissivity and high reflectivity. The shape of the inner surface 83 of baffle 27 is designed to minimize or prevent any reflection or multi-reflection of radiation from incident on the sensitive area 47 of the detector element 23.

In one embodiment, the inner surface 83 of baffle 27 forms a spherical surface, the center of the sphere coinciding with the center of the detector sensitive area 47, enclosing the detector element 23. An opening 95 is formed in the portion of the sphere over and opposite the sensitive area 47. The dimensions of the opening 95 are sufficient to allow the beam 45 (as shown in FIG. 2) to be incident on the sensitive area 47 and minimize or prevent any stray radiation from reaching the detector sensitive area 47. The front surface 89 of the detector element 23, the exposed surface 87 of retainer ring 81 and the exposed portion 85 of detector base 25 within the sphere are coated with a suitable material, such as a suitable black coating, for example, to create a radiation trap for any stray radiation. Thermistor 63 measures the temperature of the baffle 27 to enable compensation for its emission effects on the substance concentration measurements.

Figure 6:
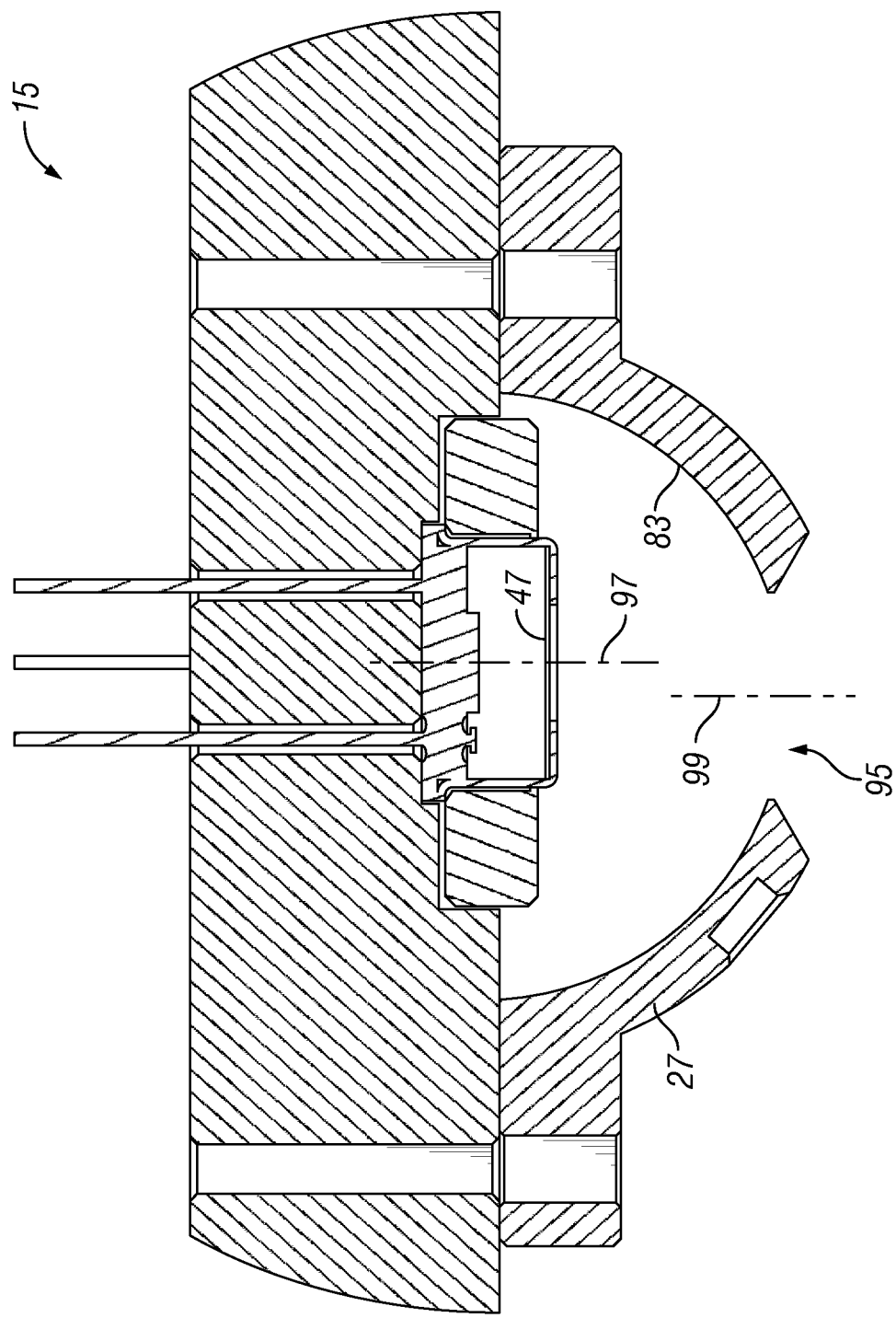

Referring now also to FIG. 6, a cross-sectional view of the detector assembly 15 and baffle 27 of the optical and detector apparatus of FIG. 2 according to another embodiment is shown. In this embodiment, as described above with reference to paragraph 0028 and FIG. 2, mirrors 29 and 31 are preferably ninety-degree (90°) off-axis parabolic mirrors coated with gold or other suitable reflective material. The inner surface 83 of baffle 27 preferably forms a spherical surface having the center 99 of the sphere positioned off center with respect to the center 97 of the detector sensitive area 47. An opening 95 is formed in the portion of the sphere over and opposite the sensitive area 47. Since the maximum of the IR energy distribution of an off-axis mirror is off center, the position of the center 99 of the baffle opening 95 is also offset from the center 97 of the detector sensitive area 27 to provide maximum IR energy collection. The dimensions of the opening 95 are sufficient to allow the beam 45 (as shown in FIG. 2) to be incident on the detector sensitive area 47 and minimize or prevent any stray radiation from reaching the detector sensitive area 47.

Although the invention has been described in terms of certain embodiments, other embodiments that are apparent to those of ordinary skill in the art, including embodiments which do not provide all of the features and advantages set forth herein, are also within the scope of this invention. Accordingly, the scope of the invention is defined by the claims that follow.

What is claimed is:

1. Apparatus for non-invasive measurement of a substance within a body, the apparatus comprising:
   a detector for sensing radiation emitted or remitted from a body;
   optics configured to focus the radiation on a sensitive area of the detector;
   a baffle attached to and in thermal contact with the detector, the baffle being disposed to at least partially surround a detector sensitive area and configured to minimize the incidence of stray radiation on the detector sensitive area,
   wherein an interior surface of the baffle opposite the detector has a high reflectivity and low emissivity, the interior surface of the baffle being formed to minimize the incidence of radiation reflection or multi-reflection on the detector sensitive area, and
   wherein the interior surface of the baffle constitutes a portion of a sphere surrounding the detector, a portion of the baffle above and opposite the sensitive area of the detector having an opening allowing the radiation to reach the sensitive area of the detector.

2. The apparatus of claim 1, further comprising one or more temperature sensors attached to one or more of a plurality of elements of the optics and to the detector, the one or more temperature sensors being configured to measure the temperature of the one or more elements of the optics and the temperature of the detector.

3. The apparatus of claim 2, wherein the temperature of the one or more of the plurality of optics elements and the temperature of the detector are matched with a set of predetermined compensation parameters stored in a look-up table for compensating for an effect on the non-invasive measurement of the temperature of each of the one or more of the plurality of optics elements and the detector, an ambient temperature and a temperature measured at a surface of the body.

4. The apparatus of claim 1, wherein an exterior surface of the baffle being coated with a suitable black coating for absorbing stray radiation.

* * * * *